(12) United States Patent
McKay

(10) Patent No.: US 8,998,854 B2
(45) Date of Patent: Apr. 7, 2015

(54) CATHETER DEVICES AND DRAINAGE SYSTEMS FOR DELIVERING THERAPEUTIC AGENTS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 642 days.

(21) Appl. No.: 12/695,899

(22) Filed: Jan. 28, 2010

(65) Prior Publication Data

US 2011/0184338 A1 Jul. 28, 2011

(51) Int. Cl.
*A61M 5/178* (2006.01)
*A61M 27/00* (2006.01)
*A61M 25/00* (2006.01)
*A61M 1/00* (2006.01)

(52) U.S. Cl.
CPC ............ *A61M 27/00* (2013.01); *A61M 25/003* (2013.01); *A61M 25/007* (2013.01); *A61M 1/0084* (2013.01); *A61M 2025/0031* (2013.01); *A61M 2025/0036* (2013.01); *A61M 2025/004* (2013.01); *A61M 25/0026* (2013.01)

(58) Field of Classification Search
USPC .................. 604/73, 317, 183, 35, 27, 43, 506
See application file for complete search history.

(56) References Cited

U.S. PATENT DOCUMENTS

| | | | |
|---|---|---|---|
| 4,525,156 A * | 6/1985 | Benusa et al. .................. | 604/28 |
| 4,820,284 A | 4/1989 | Hauri | |
| 4,855,335 A | 8/1989 | Neperud | |
| 5,236,426 A | 8/1993 | Schottes et al. | |
| 2003/0171954 A1 | 9/2003 | Guerin et al. | |
| 2004/0054338 A1 | 3/2004 | Bybordi et al. | |
| 2005/0043673 A1 * | 2/2005 | Lieberman ...................... | 604/28 |
| 2005/0107756 A1 | 5/2005 | McCraw | |

(Continued)

FOREIGN PATENT DOCUMENTS

| DE | 1955059 | * | 2/1967 |
|---|---|---|---|
| DE | 1955059 U | | 2/1967 |

(Continued)

OTHER PUBLICATIONS

International Search Report and Written Opinion for PCT/US2011/023042 the counterpart application mailed on Oct. 31, 2011.
European Search Report for PCT2011/0184338A1 the counterpart application mailed on Jun. 4, 2013.

*Primary Examiner* — Kevin C Sirmons
*Assistant Examiner* — Deanna K Hall
(74) *Attorney, Agent, or Firm* — Sorrell Lenna & Schmidt LLP

(57) ABSTRACT

A catheter for drainage of a wound and delivery of a therapeutic agent at or near the wound of a patient is provided. The catheter comprises: a proximal end configured to receive the therapeutic agent and permit passage of bodily fluid, the proximal end configured to be coupled to a drainage tube and/or a therapeutic agent delivery device; a distal end for insertion at or near the wound; and a body disposed between the proximal end and distal end of the catheter and configured to receive the therapeutic agent from the proximal end of the catheter, the body having a first set of holes configured to allow passage of the therapeutic agent from the proximal end to a site at or near the wound and the body having a second set of holes configured to allow drainage of bodily fluid from the wound into the catheter.

11 Claims, 4 Drawing Sheets

(56) References Cited

U.S. PATENT DOCUMENTS

2007/0106247 A1  5/2007  Burnett et al.
2009/0177141 A1  7/2009  Kucklick

FOREIGN PATENT DOCUMENTS

WO    2008067362 A2    6/2008
WO    2009049823 A1    4/2009

* cited by examiner

CATHETER DEVICES AND DRAINAGE SYSTEMS FOR DELIVERING THERAPEUTIC AGENTS

BACKGROUND

During or after surgery, patients may require a wound drainage system or catheter to allow unnecessary body fluids or air to flow out of the body from a surgical wound. A drainage system or catheter can be inserted while the patient is in the operating room receiving general anesthesia. By using a drainage system or catheter to remove fluid and/or blood from or near a wound, the wound can heal faster without as much risk of an infection.

Catheters have long been used to drain unnecessary body fluids or air. Catheters are generally hollow flexible tubes made of plastic or rubber for insertion into a body cavity, duct or vessel to allow the passage of fluids or distend a passageway. The other end of the catheter is generally connected to a collection device such as a drainage bag, plastic bulb or plastic carton.

Sometimes, wounds are treated with therapeutic agents during surgery for one or more reasons, for example, to prevent, reduce and/or treat post-operative pain and/or inflammation, to prevent infections from developing at the wound site, etc. There may be a need to systemically or locally administer additional therapeutic agents following surgery to provide additional treatment. Also, when a drain or catheter is used, the therapeutic agent or some of it may migrate with unnecessary body fluids from the wound site through the drain or catheter to a collection device thereby necessitating the administration of additional therapeutic agent to the wound site. Accordingly, there is a need for a device to drain unnecessary body fluids or air from a wound site while also administering therapeutic agents.

SUMMARY

New catheters that drain unnecessary body fluids or air from or near a wound site while also administering therapeutic agents are provided. In various embodiments, new catheters are provided that effectively drain unnecessary body fluids from or near a wound site while administering therapeutic agents to the wound site simultaneously, sequentially or as desired.

In one embodiment, a catheter for drainage of a wound and delivering a therapeutic agent at or near the wound of a patient is provided. The catheter comprises: a proximal end configured to receive the therapeutic agent and permit passage of bodily fluid; a distal end for insertion at or near the wound; and a body disposed between the proximal end and distal end of the catheter and configured to receive the therapeutic agent from the proximal end of the catheter. The proximal end can be configured to be coupled to a drainage tube, a collection container and/or a therapeutic agent delivery device. The body can have a first set of holes configured to allow passage of the therapeutic agent from the proximal end to a site at or near the wound and the body can have a second set of holes configured to allow drainage of bodily fluid from or near the wound into the catheter.

The catheter in some embodiments may comprise a channel disposed throughout the proximal end, the body and the distal end of the catheter wherein the channel is fluidly connected to the first and second set of holes, and the channel is configured to allow passage of therapeutic agent from the proximal end through the body and out of the first set of holes to the site at or near the wound and allow entrance of bodily fluid from the second set of holes into the body and out the proximal end of the catheter wherein the first set of holes and the second set of holes can have the same (thereby essentially being one set of holes) or different diameters.

The catheter may in some embodiments comprise at least two channels disposed throughout the proximal end, the body and the distal end of the catheter wherein the first channel is fluidly connected to the first set of holes and configured to allow passage of therapeutic agent from the proximal end through the body and out of the first set of holes to the site at or near the wound, and the second channel is fluidly connected to the second set of holes and configured to allow entrance of bodily fluid from the second set of holes into the body and out the proximal end of the catheter.

The first set of holes for therapeutic agent delivery may have a smaller diameter than the second set of holes for drainage of bodily fluid or the first set of holes for therapeutic agent delivery may have a larger diameter than the second set of holes for drainage of bodily fluid. In some embodiments, the first set and second set of holes can be uniformly disposed on a surface of the body.

The proximal end of the catheter in some embodiments may be coupled to a collection container outside of the patient's body and the collection container may be coupled to a pump that draws bodily fluid into the collection container and delivers the therapeutic agent from the collection container to or near the wound. The proximal end of the catheter in some embodiments may be coupled to a drainage tube coupled to a collection container outside of the patient's body. In some embodiments, the drainage tube can be coupled to a pump that draws bodily fluid into the collection container and delivers the therapeutic agent from the collection container to or near the wound.

In some embodiments, (i) the proximal end of the catheter may be coupled to a drainage tube which is coupled to a collection container outside of the patient's body and the proximal end of the catheter may be coupled to a therapeutic agent delivery tube having at least one port for administration of a therapeutic agent, or (ii) the proximal end of the catheter may be coupled to a tube which is coupled to a collection container outside of the patient's body that allows bodily fluids to pass through it into the collection container and the tube comprises at least one port for administration of a therapeutic agent through the tube and into at least the proximal end of the catheter. The tube may be coupled to a pump that draws bodily fluid into the collection container solely or also delivers the therapeutic agent to or near the wound at different time intervals or simultaneously or the tube may comprise two lumens, one lumen for drainage of the bodily fluid and a second lumen for delivery of the therapeutic agent to the wound at the same or different time periods. In some embodiments, the tube can be an extension of the catheter. The tube when coupled to a pump can also have a valve to shut off drainage of bodily fluid so that therapeutic agent can be delivered. In some embodiments where the tube comprises two lumens as described above, the lumen for drainage can have a valve which can be closed to make sure there is no drainage of bodily fluid if desired.

In another embodiment, a system for drainage of a wound and delivering a therapeutic agent at or near the wound of a patient is provided. The system comprises a catheter, a tube and at least one port connected to the tube. The catheter has a proximal end configured to receive the therapeutic agent and permit passage of bodily fluid and configured to be coupled to a drainage tube and/or a therapeutic agent delivery device. The catheter has a distal end for insertion at or near the wound. The catheter has a body disposed between the proximal end and distal end of the catheter and configured to receive the therapeutic agent from the proximal end of the catheter. The body has a first set of holes configured to allow passage of the therapeutic agent from the proximal end to a site at or near the wound and a second set of holes configured to allow drainage of bodily fluid from or near the wound. The tube has a first end and a second end wherein the first end is coupled to the proximal end of the catheter and the second end of the tube is coupled to a collection container and a delivery device of the therapeutic agent to the catheter. The tube can have a lumen configured to allow bodily fluids to pass through it to the collection container, and the at least one port connected to the tube may be connected between the first and second end for administration of a therapeutic agent through the tube and into at least the proximal end of the catheter and through the first set of holes. A syringe may be coupled to the at least one port by a luer fitting wherein the syringe has a plunger that allows delivery of the therapeutic agent by forward movement of the plunger. The tube may be coupled to a pump that applies vacuum pressure to draw bodily fluid into the collection container and pressure to deliver the therapeutic agent to or near the wound. Drainage and therapeutic agent delivery can alternate back and forth at appropriate times or simultaneously. Therefore, either the vacuum pump is temporarily shut off or a valve in the tube is closed while injecting the therapeutic drug and waiting for it to take effect. In some embodiments, the tube may comprise two lumens wherein the first lumen is for receiving the bodily fluid from the catheter and a second lumen is for delivery of the therapeutic agent to the catheter, and the first lumen is aligned with the second set of holes and the second lumen is aligned with the first set of holes.

The catheter may comprise a channel disposed throughout the proximal end, the body and the distal end of the catheter wherein the channel is fluidly connected to the first and second set of holes, and the channel is configured to allow passage of therapeutic agent from the proximal end through the body and out of the first set of holes to or near the wound and allow entrance of bodily fluid from the second set of holes into the body and out the proximal end of the catheter to the tube wherein the first set of holes and the second set of holes can have the same (thereby essentially being one set of holes) or different diameters.

The catheter may in some embodiments comprise at least two channels disposed throughout the proximal end, the body and the distal end of the catheter wherein the first channel is fluidly connected to the first set of holes and configured to allow passage of therapeutic agent from the proximal end through the body and out of the first set of holes to or near the wound, and the second channel is fluidly connected to the second set of holes and configured to allow entrance of bodily fluid from the second set of holes into the body and out the proximal end of the catheter to the tube leading to the collection container.

Yet another embodiment provides for a method of draining a wound and delivering a therapeutic agent at or near the wound. The method comprises: inserting a catheter at or near the wound, the catheter having a proximal end configured to receive the therapeutic agent and permit passage of bodily fluid, the proximal end configured to be coupled to a tube and/or a therapeutic agent delivery device, the catheter having a distal end for insertion at or near the wound, the catheter having a body disposed between the proximal end and distal end of the catheter and configured to receive the therapeutic agent from the proximal end of the catheter, the body having a first set of holes configured to allow passage of the therapeutic agent from the proximal end to a site at or near the wound and a second set of holes configured to allow drainage of bodily fluid from or near the wound and the proximal end of the catheter connected to the tube having a first end and a second end, the first end coupled to the proximal end of the catheter, the second end of the tube coupled to a collection container, the tube having a lumen configured to allow bodily fluids to pass through it to the collection container; and injecting the therapeutic agent into at least one port connected to the tube between the first and second end so that the therapeutic agent passes through the tube and into at least the proximal end of the catheter and through the first set of holes to or near the wound. In some embodiments, the tube can be an extension of the catheter. The wound may be a surgical wound and the therapeutic agent may be an analgesic agent, anti-inflammatory agent, antimicrobial agent and/or irrigation fluid. The catheter and/or collection container may be inserted below the wound so that gravity will draw fluid into the catheter.

The catheter in the various embodiments may be flexible and flat or tubular shaped.

The therapeutic agent in the various embodiments can comprise an anti-inflammatory agent, analgesic agent, and/or antimicrobial agent that irrigates the wound.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
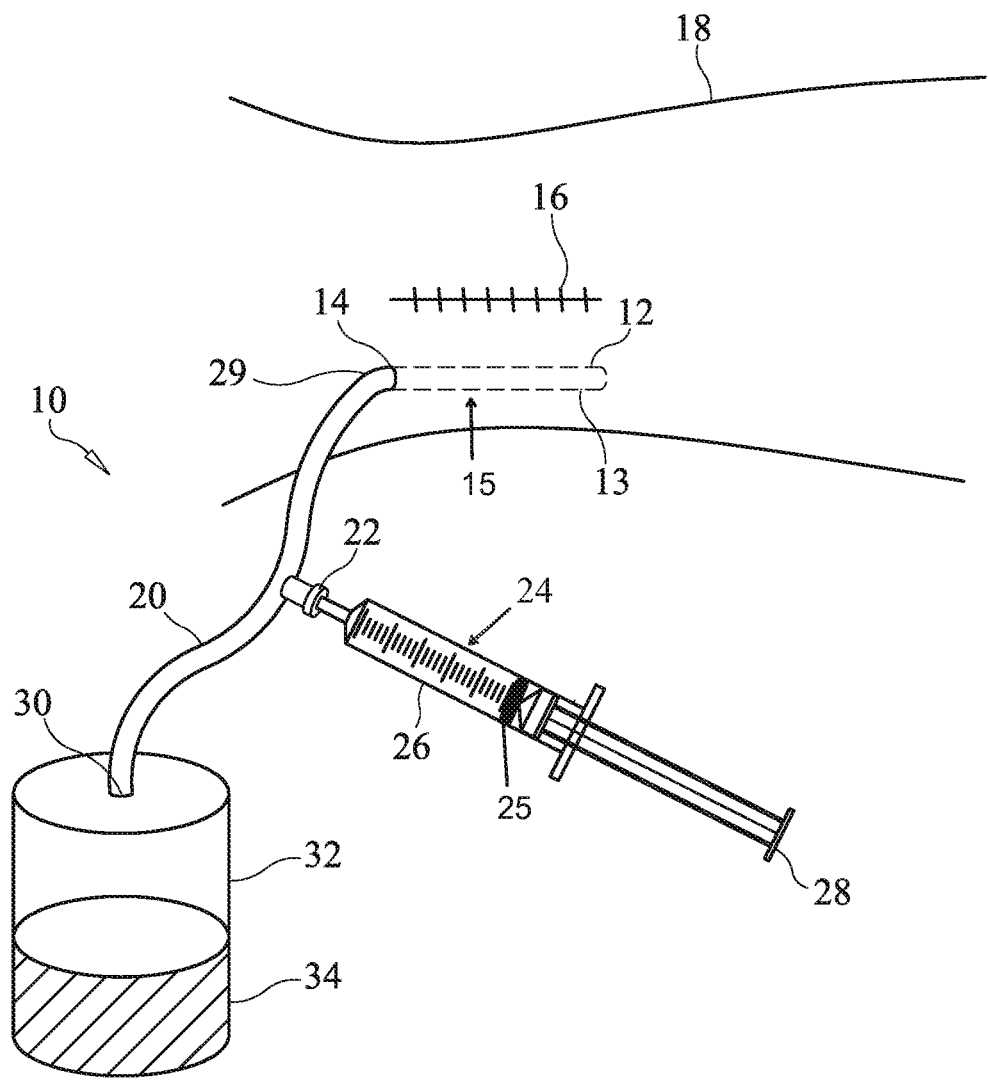
FIG. 1 is a front view embodiment of a drainage and drug delivery system comprising a catheter for drainage of a wound and delivery of a therapeutic agent, a drainage tube, a therapeutic agent delivery device and a collection container.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a catheter" includes one, two, three or more catheters.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Therapeutic Agent

The term "drug" as used herein is generally meant to refer to any substance that alters the physiology of a patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs.

Examples of drugs suitable for administration in the catheter, include, but are not limited to an anti-inflammatory agent, analgesic agent, anti-infective agents, or osteoinductive growth factor or a combination thereof. Anti-inflammatory agents include, but are not limited to, salicylates, diflunisal, indomethacin, ibuprofen, naproxen, tolmetin, keterolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Suitable analgesics also include agents with analgesic properties, such as for example, amitriptyline, carbamazepine, gabapentin, pregabalin, clonidine, or a combination thereof.

Exemplary anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin;

clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Unless otherwise specified or apparent from context, where this specification and the set of claims that follow refer to a drug (e.g., an anti-inflammatory agent, analgesic, and the like), the inventor is also referring to a pharmaceutically acceptable salt of the drug including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids or the like.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing" includes a decrease in the symptom or condition and does not require complete alleviation of signs or symptoms, and does not require a cure.

The drug or drugs administered using a delivery device to a site at or near a wound via a catheter are prepared as an injectable formulation that can be loaded into the delivery device.

FIG. 1 is a front view embodiment of a drainage and drug delivery system 10 comprising a catheter 15 for drainage from a nearby wound and/or incision 16 and delivery of a therapeutic agent 25, a drainage tube 20, a therapeutic agent delivery device 24 and a collection container 32. The catheter 15 is placed during a surgical procedure at or nearby a wound or incision 16 through the skin 18 for typically one to three days post-surgery. The catheter 15 in this embodiment comprises a proximal end 14, a distal end 12 and a body 13 disposed between the proximal end 14 and the distal end 12. The proximal end 14 is configured to be coupled to a drainage tube 20. The drainage tube 20 has a first end 29, a second end 30 and a port 22 for receipt or coupling of a therapeutic agent delivery device 24. The second end 30 of the drainage tube 20 drains unnecessary bodily fluid 34 from or near the wound into a collection container 32. The therapeutic agent delivery device 24 includes a barrel 26 holding therapeutic agent 25 and a plunger 28. As the plunger 28 is pushed in, therapeutic agent 25 is pushed into the drainage tube 20 via port 22, and then towards the first end 29 of the drainage tube 20 into the proximal end 14, body 13 and distal end 12 of the catheter 15.

Figure 2A:
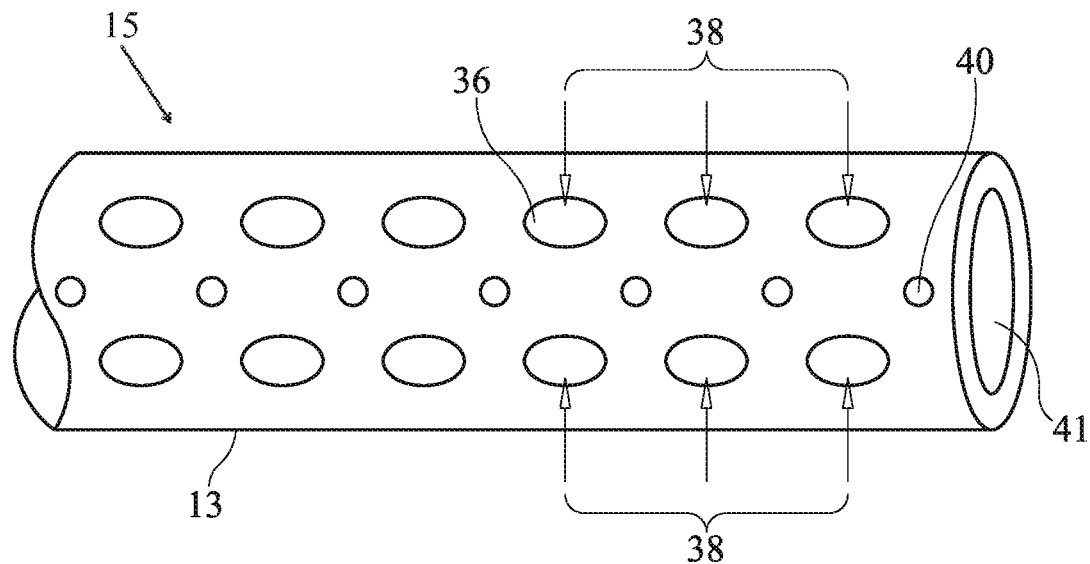
FIG. 2A is a front view of a catheter for drainage of a wound and delivery of a therapeutic agent.
Figure 2B:
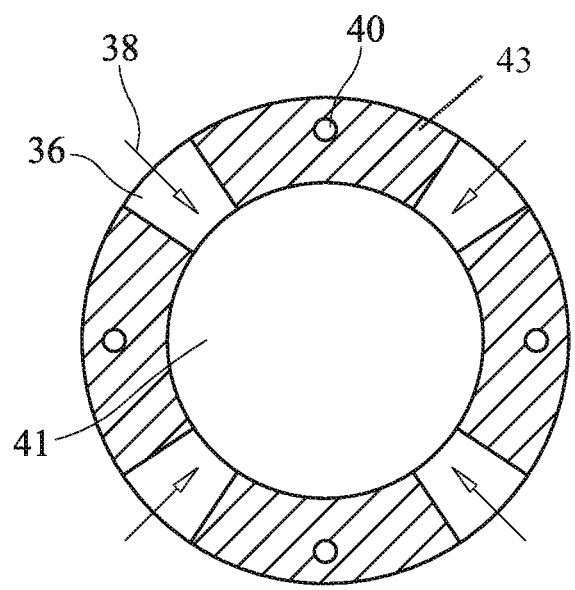
FIG. 2B is a cross-sectional view of the distal portion of the catheter shown in FIG. 2A.

The drainage tube 20 and the catheter 15 may have drug channels 43 (as shown in the embodiment of FIG. 2B) for carrying the therapeutic agent 25 through the drainage tube 20 and the catheter 15. The body 13 has a first set of holes 40 (see FIG. 2A) from the proximal end 14 to the distal end 12 of the catheter 15 which allow the passage of therapeutic agent 25 to or near the wound. Therapeutic agent 25 released via holes 40 near the distal end 12 of the catheter 15 may be released closer to or at the wound. The body 13 also has a second set of holes 36 (see FIG. 2B) configured to allow drainage of bodily fluid 34 from or near the wound into the catheter 15. The proximal end 14 permits passage of bodily fluid 34 into the drainage tube 20 at its first end 29 to the second end 30 of the drainage tube 20 and into the collection container 32.

In some embodiments, the collection container may be coupled to a drainage tube outside of the patient's body and the collection container may be coupled to a pump that draws bodily fluid into the collection container and delivers the therapeutic agent to or near the wound. A therapeutic agent delivery device is not necessary in such embodiments as the collection container holds and delivers the therapeutic agent to or near the wound via the pressure from the pump. The pump can draw bodily fluid into the collection container and deliver the therapeutic agent to or near the wound at different time intervals or the tube may comprise two lumens, one lumen for drainage of the bodily fluid and a second lumen for delivery of the therapeutic agent to the wound at the same or different time periods.

FIG. 2A is a front view of one embodiment of a catheter 15. The catheter 15 comprises a channel 41 disposed throughout the proximal end 14, the body 13 and the distal end 12 wherein the channel 41 is fluidly connected to the second set of holes 36 to allow drainage 38 of bodily fluid from or near the wound through the second set of holes 36 into the channel 41. The bodily fluid then moves down the channel 41 through the body 13 and out the proximal end 14 of the catheter 15. The body 13 also comprises a first set of holes 40 which allow passage of therapeutic agent (not shown in FIG. 2A) at or near the wound. Therapeutic agent can flow from the proximal end 14 to the first set of holes 40 on the body 13 via drug channels 43 (see FIG. 2B).

In some embodiments, the channel carries therapeutic agent from the proximal end through the body and out of the first set of holes at or near the wound or incision and the channel carries bodily fluid from the second set of holes through the body and out the proximal end of the catheter. Therapeutic agent can be carried to the first set of holes from a delivery device (e.g., a syringe) by action of the pressure from pushing in a plunger on a delivery device for example. After the therapeutic agent is delivered at or near the wound, unnecessary bodily fluid will drain via the second set of holes into the channel. The catheter can comprise means to close the second set of holes when therapeutic agent is delivered at or near the wound via the first set of holes. In some embodiments, each of the second set of holes can comprise a check valve which will prevent drainage of bodily fluid into the channel when therapeutic agent is carried to the first set of holes via the pressure from the delivery device.

In some embodiments, the catheter may comprise at least two channels disposed throughout the proximal end, the body and the distal end wherein the first channel is fluidly connected to the first set of holes which allow passage of therapeutic agent from the first channel to or near the wound, and the second channel is fluidly connected to the second set of holes which allow entrance of bodily fluid from or near the wound into the second channel and down the body and out the proximal end of the catheter.

As is apparent in FIG. 2A, the first set of holes 40 for therapeutic agent delivery may have a smaller diameter than the second set of holes 36 for drainage of bodily fluid. It will be understood by those skilled in the art that the first set of holes 40 for therapeutic agent delivery can have in some embodiments a larger diameter than the second set of holes 36 for drainage of bodily fluid. The first set and second set of holes, 40 and 36, are uniformly disposed on the surface of the body 13, however, it will be understood by those skilled in the art that the first set and second set of holes, 40 and 36, can be disposed on the surface of the body 13 in other patterns or as desired.

FIG. 2B is a cross-sectional view of the distal portion of the body 13 of the catheter 15 shown in FIG. 2A. The body 13 has a first set of holes 40, a second set of holes 36, drug channels 43 and a channel 41. Bodily fluid 34 at or near a wound drains (as shown by reference numeral 38) into the channel 41 of the body 13 via the second set of holes 36 and flows in the channel 41 down the proximal end of the catheter 15 and out the catheter 15 into a collection container (not shown). Therapeutic agent (not shown) flows into the proximal end of the catheter 15 through the body 13 and into the distal end 12 of the catheter 15 via drug channels 43. Therapeutic agent is then released at or near the wound 16 via the first set of holes 40.

Figure 3:
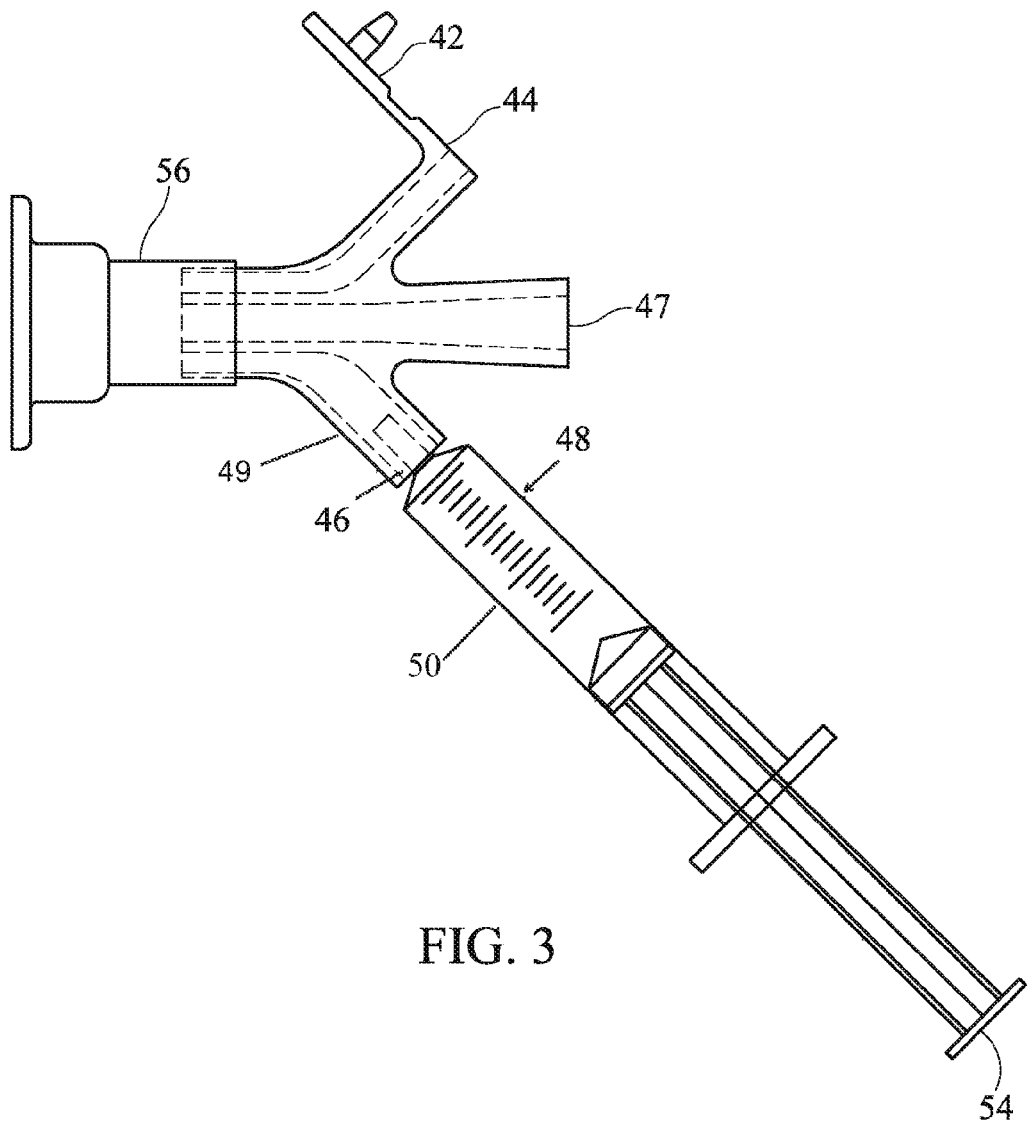
FIG. 3 is a front view of a port which can be connected to a drainage tube or catheter wherein the port comprises three ports for administration of a therapeutic agent.

FIG. 3 is a front view of a port which can be connected to a drainage tube or catheter wherein the port comprises three ports for administration of a therapeutic agent. The three ports shown in FIG. 3 are the first port 49, the second port 47 and the third port 44. The third port 44 has a cap 42 attached therewith which can be used to close the third port 44. Each of the three ports is coupled to a lumen (shown by dotted lines) for receipt of therapeutic agents and the lumens form together a trilumen tubing 56 which empties into a drainage tube or catheter. The first port is coupled to a drug delivery device 48 via a luer lock 46. The drug delivery device 48 comprises a barrel 50 which holds the therapeutic agent (not shown) and a plunger 54. As the plunger 54 is pushed inward, therapeutic agent inside the barrel 50 is pushed into the first port 49 and through the trilumen tubing 56 and toward or into the catheter for delivery at or near the wound.

Figure 4:
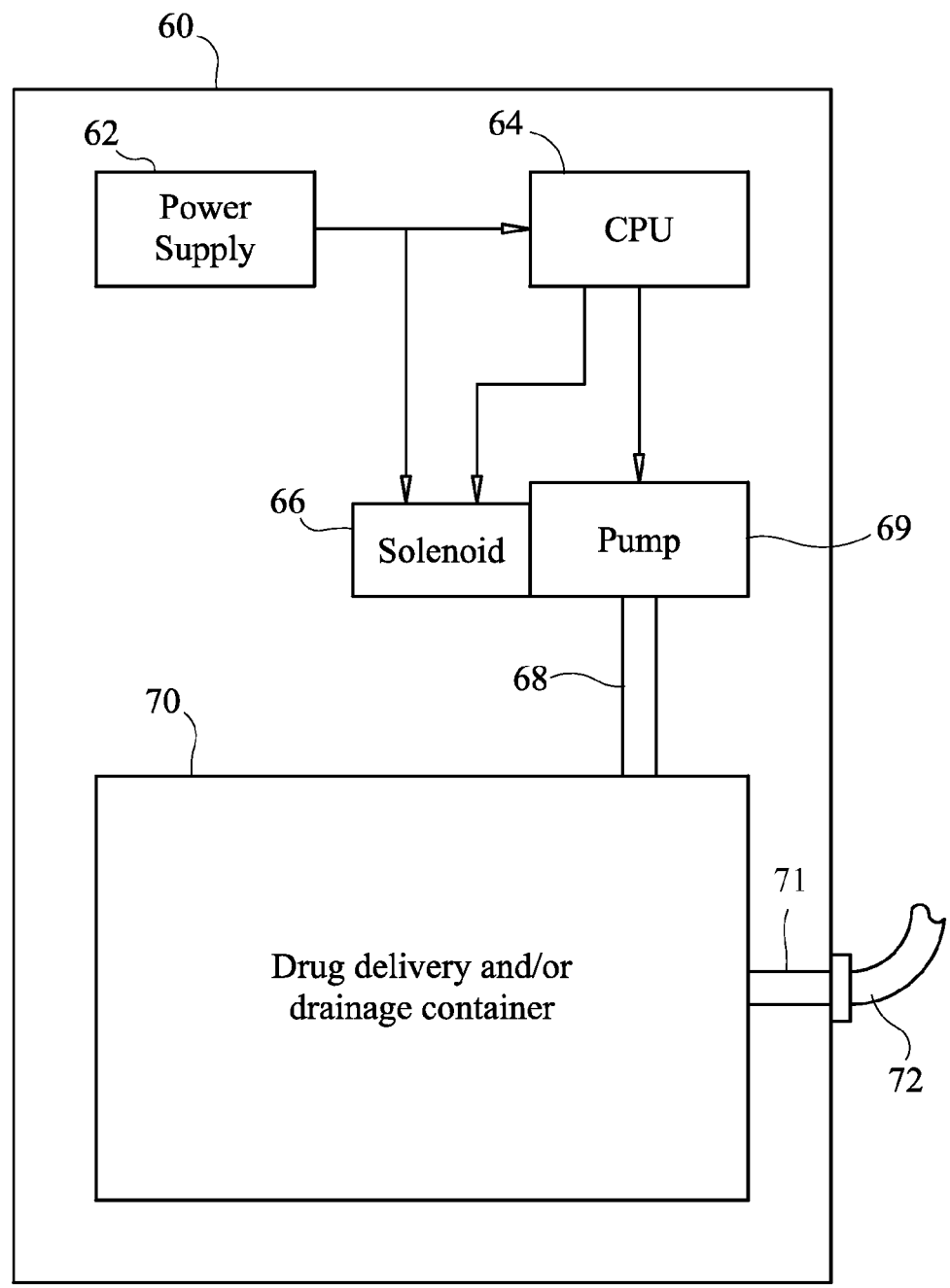
FIG. 4 is a block diagram illustrating a pump and suction unit for use with a catheter or drainage tube for collecting unnecessary bodily fluid from or near a wound and delivery of a therapeutic agent to or near the wound.

FIG. 4 is a block diagram illustrating a pump and suction unit 60 for use with a catheter tube 72 for collecting unnecessary bodily fluid from or near a wound and delivery of a therapeutic agent to the wound. The pump and suction unit 60 has a power supply 62 to provide power to its components. The pump and suction unit 60 includes a CPU 64 which controls a solenoid 66 and a pump 69. The CPU 64 allows for a patient or medical care provider to turn on and off the pump 69 thereby controlling the application of vacuum or the delivery of the therapeutic agent. The CPU 64 may be a microprocessor, controller or other specialized circuitry. The pump 69 can also be turned on and off under control of the CPU 64 by solenoid 66. The pump 69 provides vacuum pressure to the drug delivery and/or drainage container 70 via conduit 68 which is attached to the pump 69. The pump 69 provides vacuum pressure to or near the wound thereby draining unnecessary bodily fluid from or near the wound via a catheter tube or tubing 72 into the drug delivery and/or drainage container 70 at entry conduit 71. Multiple compartments for holding therapeutic agent and unnecessary bodily fluid separately are not shown in container 70, however, it will be understood by those skilled in the art that container 70 may comprise such multiple compartments and the CPU 64 can control the interface of each compartment with the catheter tubing 72 as well as the vacuum pressure from the pump 69 via conduit 68. In some embodiments, the catheter tubing 72 may comprise two channels, one carrying therapeutic agent from the container 70 to or near the wound and the other carrying bodily fluid from or near the wound to the container 70. Both channels will be connected to a respective compartment of container 70.

Sterilization

The components of a drainage and drug delivery system (e.g., a catheter, drainage tube, drug delivery device or syringe, collection device, etc.) may be sterilizable. In various embodiments, one or more components of the system can be sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the components. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of a drainage and drug delivery catheter system. E-beam radiation comprises a form of ionizing energy, which is generally characterized by low penetration and high-dose rates. E-beam irradiation is similar to gamma processing in that it alters various chemical and molecular bonds on contact, including the reproducing cells of microorganisms. Beams produced for e-beam sterilization are concentrated, highly-charged streams of electrons generated by the acceleration and conversion of electricity.

Other methods may also be used to sterilize a drainage and drug delivery system and/or one or more components of the drainage and drug delivery system, including, but not limited to, gas sterilization, such as, for example, with ethylene oxide or steam sterilization.

Kits

In various embodiments, a kit is provided that may include additional parts along with the drainage and drug delivery catheter system. The kit may include the drainage and drug delivery catheter, a drainage tube and a collection device in a first compartment. The second compartment may include one or more drug delivery devices loaded with a therapeutic agent and any other instruments needed for administration of a therapeutic agent. A third compartment may include gloves, drapes and other procedural supplies for maintaining sterility during the drainage and drug delivery process, as well as an instruction booklet. A fourth compartment may include additional cannulas, needles and/or syringes. Each tool may be separately packaged in a plastic pouch that is radiation sterilized. A cover of the kit may include illustrations of the procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A catheter for drainage of a wound and delivering a therapeutic agent at or near the wound of a patient, the catheter comprising: a proximal end configured to receive the therapeutic agent and permit passage of bodily fluid, the proximal end configured to be coupled to a drainage tube and a therapeutic agent delivery device; a distal end for insertion at or near the wound; and a body disposed between the proximal end and distal end of the catheter and configured to receive the therapeutic agent from the proximal end of the catheter, the body having a first set of holes configured to allow passage of the therapeutic agent from the proximal end to a site at or near the wound and the body having a second set of holes configured to allow drainage of bodily fluid from the wound into the catheter, wherein the first set of holes is disposed on at least a first, second and third region of the catheter and the second set of holes is disposed on at least a fourth, fifth and sixth region of the catheter in an alternating arrangement, and the first set of holes is a different diameter than the second set of holes, and the proximal end of the catheter is coupled to a drainage tube which is coupled to a collection container and to at least three ports disposed between the catheter and the collection container, wherein each port of the at least three ports being coupled to a lumen forming a trilumen tubing, at least one of the ports having a cap configured to close one of the at least three ports, each lumen of the trilumen tubing being fluidly connected to a different drug channel of the drainage tube such that therapeutic agents originating from each of the at least three ports are released from the first set of holes in different regions of the catheter.

2. A catheter device for drainage of a wound and delivering a therapeutic agent according to claim 1, wherein (i) the first set of holes for therapeutic agent delivery have a smaller diameter than the second set of holes for drainage of bodily fluid or (ii) the first set of holes for therapeutic agent delivery have a larger diameter than the second set of holes for drainage of bodily fluid.

3. A catheter device for drainage of a wound and delivering a therapeutic agent according to claim 1, wherein the first set and second set of holes are uniformly disposed on a surface of the body.

4. A catheter device for drainage of a wound and delivering a therapeutic agent according to claim 1, wherein the catheter is flexible and flat or tubular shaped.

5. A catheter device for drainage of a wound and delivering a therapeutic agent according to claim 1, wherein the drainage tube is coupled to a pump that either draws bodily fluid into the collection container and/or delivers the therapeutic agent to the wound.

6. A catheter device for drainage of a wound and delivering a therapeutic agent according to claim 1, wherein the tube is coupled to a pump that draws bodily fluid into the collection container and delivers the therapeutic agent to the wound at different time intervals or simultaneously or the tube comprises two lumens, one lumen for drainage of the bodily fluid and a second lumen for delivery of the therapeutic agent to the wound at the same or different time periods, the second lumen comprising at least three drug channels corresponding to each of the three lumens of the at least three ports and the at least three drug channels being in alignment with the first set of holes in the first, second and third regions of the catheter.

7. A catheter device for drainage of a wound and delivering a therapeutic agent according to claim 1, wherein the therapeutic agent comprises an anti-inflammatory agent, analgesic agent, and/or antimicrobial agent that irrigates the wound.

8. A system for drainage of a wound and delivering a therapeutic agent at or near the wound of a patient, the system comprising: a catheter having a proximal end configured to receive the therapeutic agent and permit passage of bodily fluid, the proximal end configured to be coupled to a drainage tube and a therapeutic agent delivery device, the catheter having a distal end for insertion at or near the wound, the catheter having a body disposed between the proximal end and distal end of the catheter and configured to receive the therapeutic agent from the proximal end of the catheter, the body having a first set of holes configured to allow passage of the therapeutic agent from the proximal end to a site at or near the wound and a second set of holes configured to allow drainage of bodily fluid from the wound; a tube having a first end and a second end, the first end coupled to the proximal end of the catheter, the second end of the tube coupled to a collection container and delivery of the therapeutic agent to the catheter, the tube having a lumen configured to allow bodily fluids to pass through it to the collection container; and at least one port connected to the tube between the first and second end for administration of a therapeutic agent through the tube and into at least the proximal end of the catheter and through the first set of holes, wherein the first set of holes is disposed on at least a first, second and third region of the catheter and the second set of holes is disposed on at least a fourth, fifth and sixth region of the catheter in an alternating arrangement, and the first set of holes is a different diameter than the second set of holes, and the at least one port is disposed between the catheter and the collection container, wherein the at least one port comprises three ports with each port being coupled to a lumen forming a trilumen tubing, at least one of the ports having a cap configured to close one of the at least three ports, each lumen of the trilumen tubing being fluidly connected to a different drug channel of the tube such that therapeutic agents originating from each of the three ports are released from the first set of holes in different regions of the catheter.

9. A system for drainage of a wound and delivering a therapeutic agent according to claim 8, wherein a syringe is coupled to at least one port by a luer fitting, the syringe having a plunger that allows delivery of the therapeutic agent by forward movement of the plunger.

10. A system for drainage of a wound and delivering a therapeutic agent according to claim 8, wherein the tube is coupled to a pump that applies vacuum pressure to either draw bodily fluid into the collection container and/or pressure to deliver the therapeutic agent to the site at or near the wound.

11. A system for drainage of a wound and delivering a therapeutic agent according to claim 8, wherein the tube comprises two lumens, the first lumen for receiving the bodily fluid from the catheter and a second lumen for delivery of the therapeutic agent to the catheter, wherein the first lumen is aligned with the second set of holes in the first second and third regions of the catheter, and the second lumen comprises at least three drug channels corresponding to each of the three lumens of the three ports and the at least three drug channels being in alignment with the first set of holes in the first, second and third regions of the catheter.

* * * * *